United States Patent [19]

Wolinsky

[11] Patent Number: 4,636,195
[45] Date of Patent: Jan. 13, 1987

[54] METHOD AND APPARATUS FOR REMOVING ARTERIAL CONSTRICTION

[76] Inventor: Harvey Wolinsky, 186 Riverside Dr., New York, N.Y. 10024

[21] Appl. No.: 720,453

[22] Filed: Apr. 4, 1985

Related U.S. Application Data

[63] Continuation of Ser. No. 558,703, Dec. 6, 1983, abandoned, which is a continuation of Ser. No. 364,908, Apr. 2, 1982, abandoned.

[51] Int. Cl.<sup>4</sup> ............................................. A61M 25/00
[52] U.S. Cl. ...................................... 604/53; 604/101; 128/348.1
[58] Field of Search .................................. 604/49–54, 604/28, 43, 96–103, 266, 265, 269; 128/325, 344, 348.1

[56] References Cited

U.S. PATENT DOCUMENTS

| | | | |
|---|---|---|---|
| 550,238 | 11/1895 | Allen, Jr. | 604/102 X |
| 2,499,045 | 2/1950 | Walker et al. | |
| 2,642,874 | 6/1953 | Keeling | 604/101 |
| 2,936,760 | 5/1960 | Gants | 604/101 |
| 3,435,826 | 4/1969 | Fogarty | |
| 3,467,102 | 9/1969 | Fogarty et al. | |
| 3,472,230 | 10/1969 | Fogarty | |
| 3,516,408 | 6/1970 | Montanti | |
| 3,640,282 | 2/1972 | Kamen et al. | |
| 3,799,173 | 3/1974 | Kamen | |
| 3,889,685 | 6/1975 | Miller, Jr. et al. | |
| 4,224,929 | 9/1980 | Furihata | 128/5 |
| 4,271,839 | 6/1981 | Fogarty et al. | |
| 4,299,226 | 11/1981 | Banka | |
| 4,404,971 | 9/1983 | LeVeen et al. | 128/348.1 |
| 4,423,725 | 1/1984 | Baran et al. | 128/207.15 |
| 4,430,083 | 2/1984 | Ganz et al. | 604/265 X |
| 4,445,892 | 5/1984 | Hossein et al. | 604/101 |

OTHER PUBLICATIONS

Admiral and Small, The Journal of Clinical Investigation, 47: 1043 (1968).
Small, Advances Int. Medicine, 16: 243 (270).
Dotter et al., "Selective Clot Lysis with Low-Dose Streptokinase", Radiology III: 31-37, Apr. 1974.

Primary Examiner—Stephen C. Pellegrino
Attorney, Agent, or Firm—Wyatt, Gerber, Shoup, Scobey and Badie

[57] ABSTRACT

A catheter is described with distal and proximate balloon segments expansible to produce a chamber around arterial plaque and a conduit for delivering solubilizing liquid into the chamber. The catheter may also contain a central expansible balloon to assist in forcing the liquid into the plaque and to compress the plaque. Several solubilizing liquids are described.

11 Claims, 3 Drawing Figures

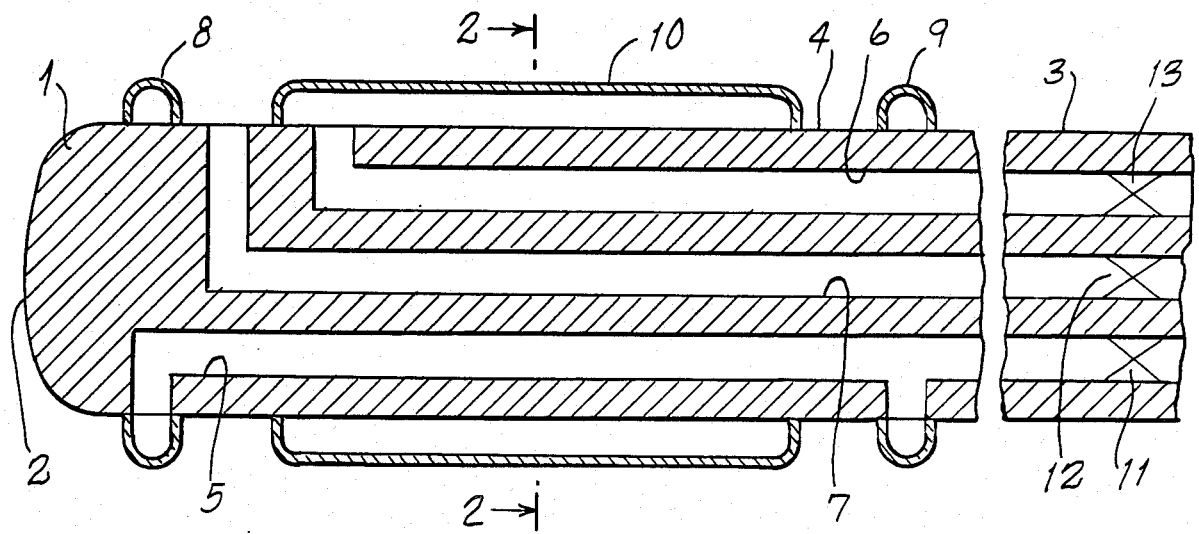
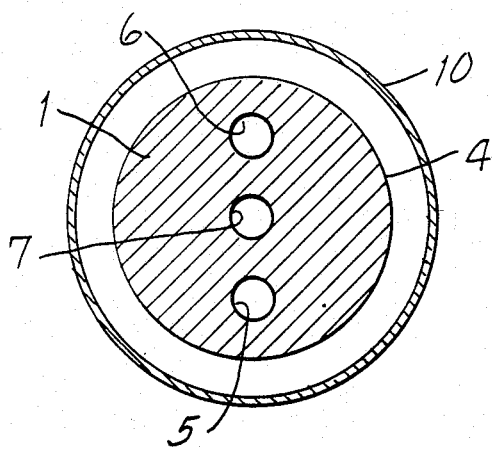
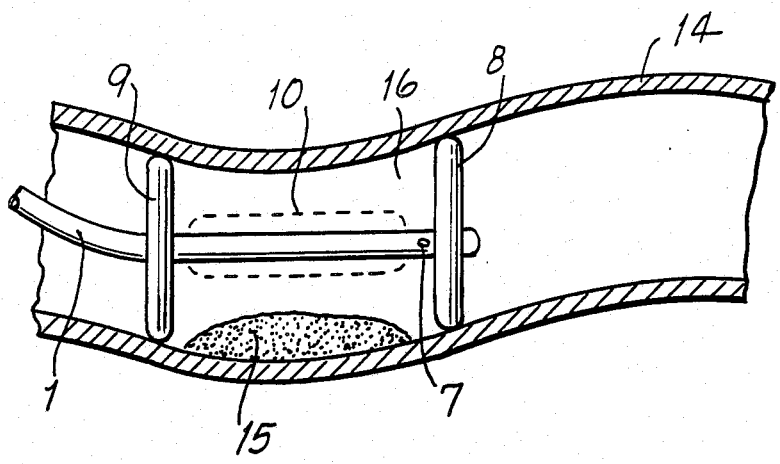

4,636,195

METHOD AND APPARATUS FOR REMOVING ARTERIAL CONSTRICTION

This application is continuation of application Ser. No. 06/558,703 filed 12/06/83, now abandoned, which is a continuation of application Ser. No. 06/364,908, filed 04/02/82, now abandoned.

BACKGROUND OF THE INVENTION

This invention relates to methods, apparatus and solutions for relieving arterial constrictions caused by deposition of plaque in arteries, particularly coronary arteries.

Recently an alternative approach to coronary bypass surgery has been developed. In this non-operative procedure for the improvement of blood flow in patients with coronary artery disease, a catheter with an inflatable balloon at the distal end is inserted into the femoral artery or by brachial cutdown, and is positioned by fluoroscopic control at the appropriate coronary ostium. The process is known as percutaneous transluminal coronary angioplasty (PTCA).

The balloon at the distal end of the catheter has a predetermined maximum diameter. It is filled with a radio opaque dye to permit visualization. Alternatively, the balloon itself may be radio opaque. When the balloon is positioned in the stenosis it is inflated for from 3 to 5 seconds and then deflated. The inflation cycle may be repeated several times to achieve satisfactory results. Normally the luminal diameter of the stenotic vessel increases at least 20% as a result of the treatment.

The procedure has been employed for treatment of single, large atherosclerotic lesions of the coronary, renal, iliac and even vertebral arteries. The effect of the expanded balloon is to literally blow open the stenotic zone. Disruption of the wall is marked, including fracture of the calcium in the lesion, tearing of the plaque itself and extravasation of plaque lipid and gruel into the adjacent vessel wall. Complications include hemorrhage, tears of the wall and sudden blockage of the damaged area with a clot. It is standard procedure to conduct the treatment with a standby surgical team. Emergency surgery is required from time to time.

The procedure is, in effect, a vigorous attack on a delicate system. However, with well selected patients in the hands of an experienced balloon team, the success rate is close to 90%. There is room for improvement. A system which would permit a less forceful attack on the plaque and on the arterial walls would generate fewer complications, increase the number of patients who could be successfully treated, and be generally more acceptable.

PTCA does not generally dissolve the plaque. It merely compresses it and forces it into the arterial wall. The total mass of the plaque is not appreciably reduced. It is, however, possible that the alteration of the atheroma structure, perhaps by redistribution of its elements, permits the eventual dissolution of at least some of the plaque. It appears that the remaining plaque body resulting from PTCA may serve as the nucleus for the formation of new plaque since restenosis has been observed in some patients.

Atherosclerotic plaques vary considerably in their composition from site to site, but certain features are common to all of them. They contain many cells, mostly these are derived from cells of the wall that have divided wildly and have grown into the surface layer of the blood vessel, creating a mass lesion. Plaques also contain cholesterol and cholesterol esters, commonly referred to as fat. This lies freely in the space between the cells and in the cells themselves. A large amount of collagen is present in the plaques, particularly advanced plaques of the type which cause clinical problems. Additionally, human plaques contain calcium to varying degrees, hemorrhagic material including clot and grumous material composed of dead cells, fat and other debris. Relatively large amounts of water are present as is typical of all tissue.

In accordance with the methods of this invention arterial constrictions are relieved, not by forcing them into the arterial wall, or by fracturing or tearing, but by dissolving at least a portion of the plaque.

THE INVENTION

This invention provides methods and apparatus for alleviation of arterial stenosis by delivery of a solubilizing liquid to the surface of the constricting plaque and into the interior thereof. As a result, at least some of the plaque components are dissolved.

The invention will be better understood from the following description and the drawings which are intended for the purpose of illustration only. In the drawings:

FIG. 1 is a schematic longitudinal sectional view of a catheter element of the invention at the distal end of a main catheter body.

FIG. 2 is a cross section taken along the line 2—2 of FIG. 1.

FIG. 3 is a view of the catheter element of FIG. 1 operatively positioned within a stenotic artery.

FIGS. 1 and 2 illustrate the solubilizing fluid delivery, balloon carrying element of the catheter of this invention. In the embodiment illustrated it comprises a main catheter body generally designated as 1 with a distal end 2 and a proximate end 3 formed with a main catheter body wall 4. The main catheter body 1 is formed with three conduits; a ring balloon expansion conduit 5, a central balloon expansion conduit 6 and a fluid delivery conduit 7. The catheter body 1 carries two ring balloons 8 and 9 at either end, and an optional central balloon 10 disposed intermediate the spaced balloons. It also carries a third conduit 7 which exits through the catheter body. Conduits 5, 6 and 7 are fitted with appropriate valves 11, 12 and 13.

The operation of a catheter of this invention is schematically illustrated in FIG. 3. In the FIG. 14 is the arterial wall of an artery constricted due to the presence of plaque body 15. The figure shows the main catheter body 1 held in place by the inflation of spaced balloons 8 and 9. The inflation of the balloons forms a chamber 16 in the artery and, as shown, surrounding the plaque. The catheter 1 is shown with the central balloon 10 in the deflated configuration. It also shows the delivery end of the third conduit 7.

In operation the catheter 1 is guided by standard procedures which may include the use of a flexible probe, a guide wire and/or a fluoroscope to a position overlaying the plaque body 15 preferably, but not necessarily, in the position shown in FIG. 3 with the distal end balloon 8 just beyond the distal end of the plaque and proximate end balloon 9 just ahead of the proximate end of the plaque. When the balloons 8 and 9 are inflated by forcing air or other fluid such as isotonic saline through valve 11 and conduit 5, the catheter is held in place by the pressure of the balloons and a chamber 16 is formed surrounding the plaque 15. The closing of valve 11 will maintain the pressure in the conduit 5 and balloons 8 and 9 so that the catheter is held in place. The position of the catheter can be checked fluoroscopically or by passing a small amount of solubilizing liquid containing a dye into the chamber. If the position is not satisfactory the pressure can be released sufficiently to slightly deflate ring balloons 8 and 9, the catheter moved in the appropriate direction, and the balloons reinflated.

Once the catheter is in place a solubilizing liquid is forced into the chamber through conduit 7. The pressure may be just sufficient to fill the chamber, i.e., from about 100 to 150 mm Hg. Alternatively it may be high enough to force some of the liquid into the plaque. Pressure of 200 to 300 mm Hg are generally sufficient for this purpose. The pressure at which the fluid is forced into the chamber may be generated by a pump upstream of valve 12. It may be augmented by expansion of the central balloon 10. This procedure has the added advantage that the expanding central balloon may compress the plaque. Thus the procedure may be combined with conventional PTCA. For this purpose the pressure may be as high as 5 to 7 atmospheres, but it will not necessarily be that high.

The central balloon 10 may be inflated after the solubilizing fluid has entered the chamber, or simultaneously with the release of the fluid into the chamber. In either event it will assist in forcing the solubilizing fluid into the plaque.

As in conventional PTCA, the catheter body may be held in place 3 to 5 seconds before deflating the balloons.

The cyclic procedure may be repeated up to 4 or more times to force as much fluid as possible into the plaque.

Preferably, however, the sequence is programed so that the inflation of the ring balloons, insertion of the solubilizing liquid and inflation of the central balloon takes place sequentially over a period of about 4 seconds. The catheter is then held in place up to a total of about 30 to 50 seconds to maximize contact of the solubilizing fluid with the plaque while controlling the interruption of blood flow at a safe level.

The catheter body can be prepared from any of a number of readily available, non-toxic, flexible polymers including, for example, polyolefins such as polyethylene or polypropylene and polyvinyl halides such as polyvinyl chloride or polyvinylidene chloride. The balloon can be fabricated from similar materials manufactured so as to be expansible under pressure and with sufficient elasticity to contract when the pressure is released. The dimensions of the balloons will be such that they will reach the desired diameter at a pressure of from about 75 to 150 mm Hg and hold the dimensions even if the pressure is increased to as high as 5 or more atmospheres.

The absolute dimensions selected for the balloons will depend upon the diameter of the arteries involved. For example, the ring balloons may be from 2 to 5 mm in length and their expanded diameters will be approximately the same. The central balloon will be of the same diameter range as the end balloons, but the length will be from about 10 to 50 mm.

The solubilizing liquid will be forced into the plaque by the application of pressure through the central conduit 7 or by the expansion of the central balloon 10. When the catheter is removed the liquid will not immediately wash out of the plaque, but will remain in the plaque in equilibrium with the arterial blood. It will be slowly replaced over the period of several hours and, as it exits the plaque, will take with it those plaque components which have dissolved in it.

A variety of solubilizing liquids are available. The liquids, of course, should be non-toxic. They should not cause clotting of the blood. Because of the low volumes involved, e.g. 0.1 to 0.5 cc, any of a number of polar organic solvents which will dissolve cholesterol and its esters, and would normally be considered too toxic for internal use can be employed. These include, for example, ether, ethanol and mixtures thereof.

Isotonic aqueous buffers containing phospholipids at a pH of from about 7.2 to 7.6 are useful. Phospholipids are naturally available compounds which on hydrolysis yield fatty acids; phosphoric acid; an alcohol, usually glycerol; and a nitrogenous base such as choline or ethanolamine. They include lecithins, cephalins and sphingomyelins. Lecithins, particularly egg lecithin, are preferred because of their easy availability and efficiency.

The efficiency of the solubilizing liquids containing egg lecithin or other phospholipid can be improved by the addition of bile acids such as cholic, deoxycholic, chenodeoxycholic, lithocholic, glycocholic and taurocholic acid.

The preferred solubilizing agents will contain at least one bile acid and at least one phospholipid in aqueous, buffered solutions at a pH of from about 7.2 to 7.6 with a total solids content of from about 10 to 30% and a water content 90 to 70% by weight. The ratio of bile acid to phospholipid by weight is from 50:50 to 85:15, preferably 60:40 to 65:35. The preferred bile acids are cholic, deoxycholic, taurocholic and glycocholic acids.

Any of a number of physiologically acceptable buffers including phosphate buffered saline, tris buffer, Ringer's lactate buffer and the like can be employed in the practice of this invention.

Especially preferred solubilizing liquids for use in this invention are buffered solutions containing phospholipid and bile acid as described above together with a collagenase, typically a mammalian collagenase, or one derived from bacteria. The collagenase concentration is normally from about 20 to 400 $\mu$g/cc of solution. The collagenase cleaves the collagen which is the main supportive structure of the plaque. The plaque body then collapses. This result together with the solubilization of the fat and other components of the plaque serves to decrease markedly the total volume of the plaque and increase the flow through of blood in the artery. The selected collagenase may be employed in aqueous buffer, such as one of those mentioned above, either with or without bile acid or phospholipid. Other proteases such as papain, or chymotrypsin may also be employed together with the collagenase or as an alternative thereto. The concentration of proteases in such solutions is from about 20 to 400 $\mu$g/cc of solution.

Other enzymes such as chondroitinase or hyaluronidase may also be employed alone or as one of the active components in the solubilizing liquid to assist in the removal of other plaque components.

What is claimed is:

1. A cathether adapted for insertion into an artery for relieving arterial constriction caused by a body of plaque comprising a main catheter body having means including two spaced balloon elements adapted to be positioned adjacent respective proximate and distal ends of the plaque body and expansible against the arterial walls for providing a chamber about said plaque body so as to hold said main catheter body in place, means carried by said main catheter body for delivering a solution into said chamber for solubilizing said plaque body, and means including a third balloon element disposed intermediate said two spaced balloon elements and expansible for forcing said solution into said plaque body while compressing said plaque body.

2. A catheter according to either claim 1, each of said two spaced balloon elements having a length ranging from about 2 mm to 5 mm and being expansible to a diameter from about 2 mm to 5 mm.

3. A catheter according to claim 1 or claim 2, said third balloon element having a length ranging from about 10 mm to 5 mm and being expansible to a diameter ranging from about 2 mm to 5 mm.

4. A catheter according to claim 1, said two spaced balloon elements being expansible by fluid pressure and adapted to remain in a stable, expanded condition at about 5 atmospheres of pressure.

5. A method for relieving a constriction in an artery caused by a body of plaque which comprises the steps of:
   1. inserting into the artery a catheter comprising a main catheter body having means including two spaced balloon elements adapted to be positioned adjacent respective proximate and distal ends of the plaque body and expansible to the arterial diameter of the constricted artery against the arterial walls for providing a chamber about said plaque body so as to hold said main catheter body in place, and means carried by said main catheter body for delivering a solution under pressure into said chamber and said plaque for solubilizing said plaque body,
   2. inflating said two spaced balloon elements,
   3. delivering a solubilizing solution into said chamber through said solution delivering means,
   4. deflating said balloon elements, and
   5. removing the catheter from the artery.

6. A method for relieving an arterial constriction caused by a body of plaque which comprises the steps of:
   1. inserting into the artery a catheter comprising a main catheter body having means including two spaced balloon elements adapted to be positioned adjacent respective proximate and distal ends of the plaque body and expansible against the arterial walls for providing a chamber about said plaque body so as to hold said main catheter body in place, means carried by said main catheter body for delivering a solutin under pressure into said chamber and said plaque for solubilizing said plaque body and means including a third expansible balloon element disposed intermediate said two spaced balloon elements,
   2. inflating said two spaced balloon elements,
   3. delivering a solubilizing solution into said chamber through said colution delivering means,
   4. inflating said third balloon element,
   5. deflating said balloon elements,
   6. removing the catheter from the artery.

7. A method as in claim 6 wherein Steps 3 and 4 are performed simultaneously.

8. A method for relieving a constriction in an artery caused by a body of plaque which comprises the steps of:
   1. inserting into the artery a catheter comprising a main catheter body having means including two spaced balloon elements adapted to be positioned adjacent respective proximate and distal ends of the plaque body and expansible to the arterial diameter of the constricted artery against the arterial walls for providing a chamber about said plaque body so as to hold said main catheter body in place, means carried by said main catheter body for delivering a solution under pressure into said chamber and said plaque for solubilizing said plaque body,
   2. inflating said two spaced balloon elements,
   3. delivering a solubilizing solution into said chamber through said solution delivering means,
   4. deflating said balloon elements, and
   5. removing the catheter from the artery; said solubilizing solution comprising an isotonic aqueous buffered mixture at a pH of from 7.2 to 7.6 of at least one phospholipid and at least one bile acid, having a solids content of from about 10% to 30% by volume and a water content of from 90% to 10% by volume the ratio of bile acid to phospholipid being from 50:50 to 85:15 by weight.

9. A method as in claim 8 wherein the phospholipid is a lecithin.

10. A method as in claim 9 wherein the bile acid is selected from the group consisting of cholic, deoxycholic, taurocholic and glycocholic acids.

11. A method as in claims 8, 9 or 10 wherein the solubilizing solution additionally contains from about 20 to 400 µg/cc of solution of collagenase.

* * * * *